(12) United States Patent
Nakaya et al.

(10) Patent No.: US 6,558,430 B1
(45) Date of Patent: May 6, 2003

(54) AIR-CYLINDER APPARATUS FOR PROSTHETIC LIMB

(75) Inventors: Yoshiaki Nakaya, Kobe (JP); Tsutomu Togashi, Kobe (JP); Masahiko Okuda, Kobe (JP); Norio Shiraishi, Kobe (JP)

(73) Assignee: Nabco Limited, Hyogo-ken (JP)

( * ) Notice: Subject to any disclaimer, the term of this patent is extended or adjusted under 35 U.S.C. 154(b) by 204 days.

(21) Appl. No.: 09/707,011

(22) Filed: Nov. 6, 2000

(30) Foreign Application Priority Data

Nov. 15, 1999 (JP) .......................................... 11-324614

(51) Int. Cl.$^7$ ................................................. A61F 2/64
(52) U.S. Cl. ........................................ 623/44; 188/313
(58) Field of Search ............................... 623/26, 39, 43, 623/44, 46; 188/301, 313, 322.13, 288

(56) References Cited

U.S. PATENT DOCUMENTS

| 3,863,274 A | | 2/1975 | Glabiszewski |
| 4,775,037 A | * | 10/1988 | Stenberg .................. 623/39 X |
| 5,344,446 A | | 9/1994 | Sawamura et al. |
| 5,405,407 A | | 4/1995 | Kodama et al. |
| 5,517,898 A | | 5/1996 | Kim et al. |
| 5,888,237 A | | 3/1999 | Shiraishi et al. |

FOREIGN PATENT DOCUMENTS

| DE | 42 33 247 A1 | 10/1992 | |
| EP | 0 837 248 A2 | 4/1998 | |
| GB | 2 282 414 A | 8/1994 | |
| GB | 2 338 653 A | 6/1998 | |
| JP | 6-197918 | 7/1994 | |
| JP | 9-201377 A | * 8/1997 | .................. 623/26 |
| JP | 11-19105 A | * 1/1999 | .................. 623/26 |
| WO | WO 95/26171 | 10/1995 | |

OTHER PUBLICATIONS

European Search Report for EP 00 30 9975 dated Mar. 5, 2001.
Patent Abstract for Japanese Patent Application No. 04359925 dated Dec. 29, 1992.

* cited by examiner

Primary Examiner—David H. Willse
(74) Attorney, Agent, or Firm—Frommer Lawrence & Haug LLP; Ronald R. Santucci

(57) ABSTRACT

There is provided an air-cylinder apparatus for use in a prosthetic limb capable of effectively adjusting the pressure characteristics over a wide range of walking speed. A second chamber 82 defined by a piston 113 is increased in pressure by air confined therein in accordance with the bending motion of the knee. Air is restricted from flowing out of the second chamber 82 by a constant throttle valve 140. In addition, the second chamber 82 is divided into plural chambers 821, 822 in accordance with increase in bending angle of the knee and air is restricted from flowing out of the newly divided chambers 821, 822 by throttle valves corresponding thereto. The division of the second chamber 82 is achieved by mutual engagement between a projection 1140b on the piston side and a recess 1127 on the bottom part of a cylinder body.

10 Claims, 20 Drawing Sheets

AIR-CYLINDER APPARATUS FOR PROSTHETIC LIMB

BACKGROUND OF THE INVENTION

This invention relates to an air-cylinder apparatus for use in a prosthetic limb designed for assisting the bending and stretching motion of an amputee's knee and more particularly to a technique capable of generating a proper resisting force in accordance with the bending motion of the knee when a prosthetic limb is in a swing phase in walking in which the prosthetic limb is left from a grounding surface such as, a floor surface.

Prosthetic limbs accompanying the bending and stretching motion of the knee are prosthetic limbs in which a femoral member and a crus member are oscillated relative to each other. Among them, there are prosthetic limbs of the type which includes an auxiliary apparatus for assisting the bending and stretching motion of the knee in order to attain a walking style (walking attitude) resembling a natural walking style. As the auxiliary apparatus, there are known a hydraulic cylinder apparatus and an air-cylinder apparatus. Comparing the two different types of cylinder apparatuses as an auxiliary apparatus, oil as working fluid of the hydraulic cylinder has almost no compressibility, while air as working fluid of the air-cylinder apparatus has compressibility. Therefore, with the use of the air-cylinder, there can be obtained a repulsive energy after the knee is bent to the maximum extent by the compressed energy generated by compression of air.

The specification of Japanese Patent Publication No. S52-47638 and FIGS. 2 and 3 of U.S. Pat. No. 5,405,407 show a first technique of an air-cylinder apparatus for use in a prosthetic limb. This technique includes a check valve within a piston and a needle valve as a throttle valve within a piston rod. Those valves are actuated to compress a chamber within the air-cylinder when the knee is bent and the flow of air out of the chamber is restricted by the throttle valve. However, the flow of air is restricted by a single throttle valve and the degree of opening of the throttle valve is kept constant during walking. For this reason, the bending motion of the knee cannot be controlled appropriately in accordance with walking speed. This follows that the first technique cannot cope with such a wide range of walking speed as slow walking, normal walking, fast walking and tripping.

In contrast, Japanese Patent No. 2,501,346 and U.S. Pat. No. 5,344,446 based thereon discloses a technique for adjusting the degree of opening of a throttle valve for restricting the flow of air in accordance with walking speed using a computer. This second technique can control the bending motion of the knee appropriately in accordance with walking speed. The wearer of the prosthetic limb can attain a natural walking attitude over a wide range of walking speed. However, this second technique has such shortcomings in that each means for controlling and driving is necessarily required for adjusting the throttle valve automatically and therefore, the prosthetic limb becomes complicated in structure and increased in cost.

In order to attain a natural walking attitude over a wide range of walking speed while restraining increase in cost, it can be contemplated to make the prosthetic limb entirely mechanically in structure without a need of a provision of a computer for controlling. A third technique, which is disclosed by National Publication No. H08-511190 (corresponding to WO95/26171) and U.S. Pat. No. 5,092, 902, can be applied to an air-cylinder apparatus, although the third technique is directed to a hydraulic cylinder apparatus and not to an air-cylinder apparatus. In the third technique, the throttle valve is provided with a plurality of throttle holes arranged in a direction of movement of a piston such that the throttle valves are sequentially closed in accordance with movement of the piston. According to this technique, resisting force against flow can be enlarged by intensifying the throttling action of the throttle valve as the bending degree of the knee is increased. However, because a throttle area is, either digitally or steppingly, varied in accordance with movement of the piston, pressure characteristics of the cylinder are also steppingly varied, thereby deteriorating the wearer's feeling of walking. Moreover, in this type of a cylinder for use in a prosthetic limb, it is necessary to adjust the pressure characteristics of the cylinder for each wearer. In the case where there is a provision of only one pressure chamber, it is difficult to meet with the requirement for adjustment of the pressure characteristics of the cylinder for each wearer.

SUMMARY OF THE INVENTION

It is, therefore, a first object of the present invention to provide an air-cylinder apparatus for use in a prosthetic limb in which pressure characteristics can effectively be adjusted over a wide range of walking speed.

It is a second object of the present invention to provide an air-cylinder apparatus for use in a prosthetic limb in which a natural walking attitude can be obtained in a wide range of walking speed without deteriorating the wearer's feeling of walking.

A third object of the present invention is to provide an air-cylinder apparatus for use in a prosthetic limb in which a throttle valve portion is stable in construction so that an accurate pressure controlling can assuredly be obtained in accordance with walking speed.

To achieve the above objects, the way the inventor(s) of the present invention thought is as follows. Basically, the interior of a cylinder body is divided into two chambers by a piston as in the related art. The divided chambers include a first chamber which is located on the head side and a second chamber which is located on the bottom side. The first and second chambers are communicated with each other through two passages. The first passage includes a first check valve for permitting a flow of air from the first chamber towards the second chamber. By permitting the flow of air from the first chamber towards the second chamber, the first passage enables the knee to be bent and besides, the first check valve confines the air, which has flowed into the second chamber, therein. The second passage includes a constant throttle valve for normally restricting a flow of air from the second chamber towards the first chamber. The constant throttle valve has the role for normally restricting the flow of air from the second chamber towards the first chamber even when the bending state of the knee is changed.

An air-cylinder apparatus for use in a prosthetic limb according to the present invention further comprises, in order to increase an internal pressure of the second chamber when the knee is bent, the following component elements.

(A) division means for dividing the second chamber, which is located on the bottom side, into plural chambers including a predetermined chamber confronting an opening for intercommunicating the second chamber with the constant throttle valve in accordance with increase in bending angle of the knee, the division means being provided at a bottom part of the cylinder body with a projection or a recess and at one surface, facing the bottom part, of the piston with a counterpart projection or a recess; and (B) an auxiliary passage for communicating each and all of the plural chambers divided by the division means only excluding the predetermined chamber with the first chamber through throttle valves, respectively.

In the air-cylinder apparatus for use in a prosthetic limb according to the present invention, it is not only arranged such that the flow of air out of the second chamber, in which air is confined in accordance with the bending motion of the knee and internal pressure is increased, by the constant throttle valve but also that the second chamber is divided into plural chambers in accordance with increase in bending angle of the knee and air is restricted from flowing out of those divided chambers by throttle valves corresponding to the divided chambers. The divided plural chambers include not only the predetermined chamber confronting the opening for communication with the constant throttle valve but also other chambers concentric therewith. In order to accurately control the pressure characteristics over a wider range of walking speed, an increased number of divisions is preferable. Actually, the number of divisions is 2 to 5 and normally, the proper number of divisions is 2 to 3. The time point for dividing the second chamber into plural chambers can properly be changed in accordance with the number of divisions. In the case where the number of divisions is 2, the time point for division is at a stage where a bending angle of the knee exceeds 40 to 60 degrees (for example, 50 degrees) for normal walking. In the case where the number of divisions is 3, the time point is not only at a stage where the bending angle exceeds, for example, 50 degrees as mentioned but also at a stage where the bending angle is smaller, for example, 30 degrees, than 50 degrees. At the respective time points, the piston and the bottom part of the cylinder body are engaged with each other through the projection and the recess, thereby defining new chambers within the second chamber. In order to hermetically close the newly defined chambers, the engagement projection and recess are provided with a seal member such as a lip type seal ring. In order to generate a higher pressure in the second chamber at the time of faster walking speed, in addition to a provision of the constant throttle valve, the second passage is preferably provided with a second check valve for permitting the flow of air from the second chamber towards the first chamber and for prohibiting the flow of air in the reversed direction.

Most preferably, the throttle valve of the auxiliary passage is communicated with the first chamber through the predetermined chamber and the constant throttle valve. By doing so, the throttle valves for the newly divided chambers defined within the second chamber are interposed between the predetermined chamber and the newly divided chambers. Since pressure is generated, under the effect of the constant throttle valve, in the predetermined chamber prior to the time point for division, pressure in the newly divided chambers is not increased abruptly. As a result, due to characteristics of the air-cylinder apparatus, a repulsive force is not generated abruptly but it is generated gradually. For this reason, the wearer of the prosthetic limb can walk with a feeling of natural walking without a sense of incompatibility.

As the constant throttle valve and the throttle valve, various kinds of throttle valves can be used. Among them, a screwing type needle valve is most preferable. The screwing type needle valve is properly adjusted in opening degree through rotation of the screw (i.e., by converting a rotary motion to a linear motion) and can be used as a fixed throttle valve having a constant throttling amount. Since the fixed throttle valve is of a construction in which no movable valve body and no spring is used, a stable controlling can be made in a movable prosthetic limb.

DETAILED DESCRIPTION OF THE EMBODIMENTS

Before describing the embodiments of the present invention, a relation between a prosthetic limb and an air-cylinder apparatus will be described with reference to FIGS. 1 to 6.

Figure 1:
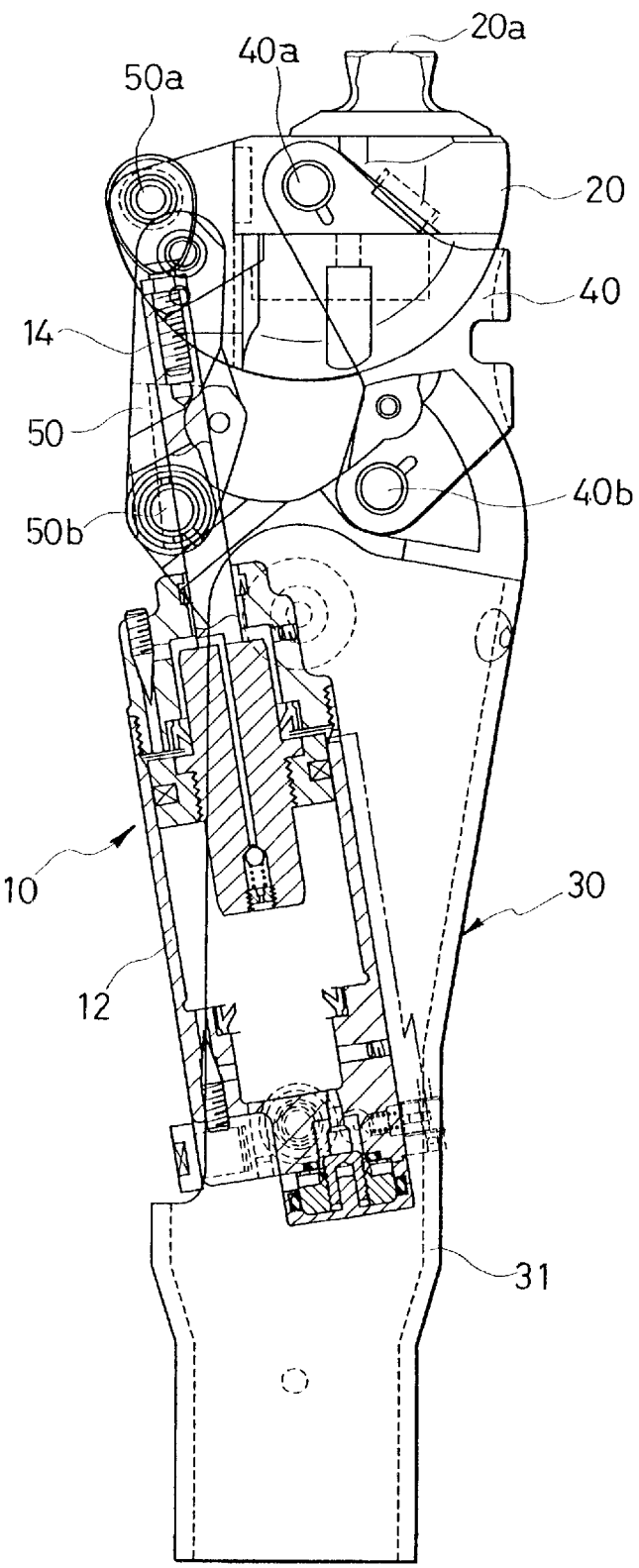
FIG. 1 is a view showing one form in which the present invention is applied to a prosthetic limb having a multi-axis knee joint and a view showing a state in which the knee is fully stretched.
Figure 2:
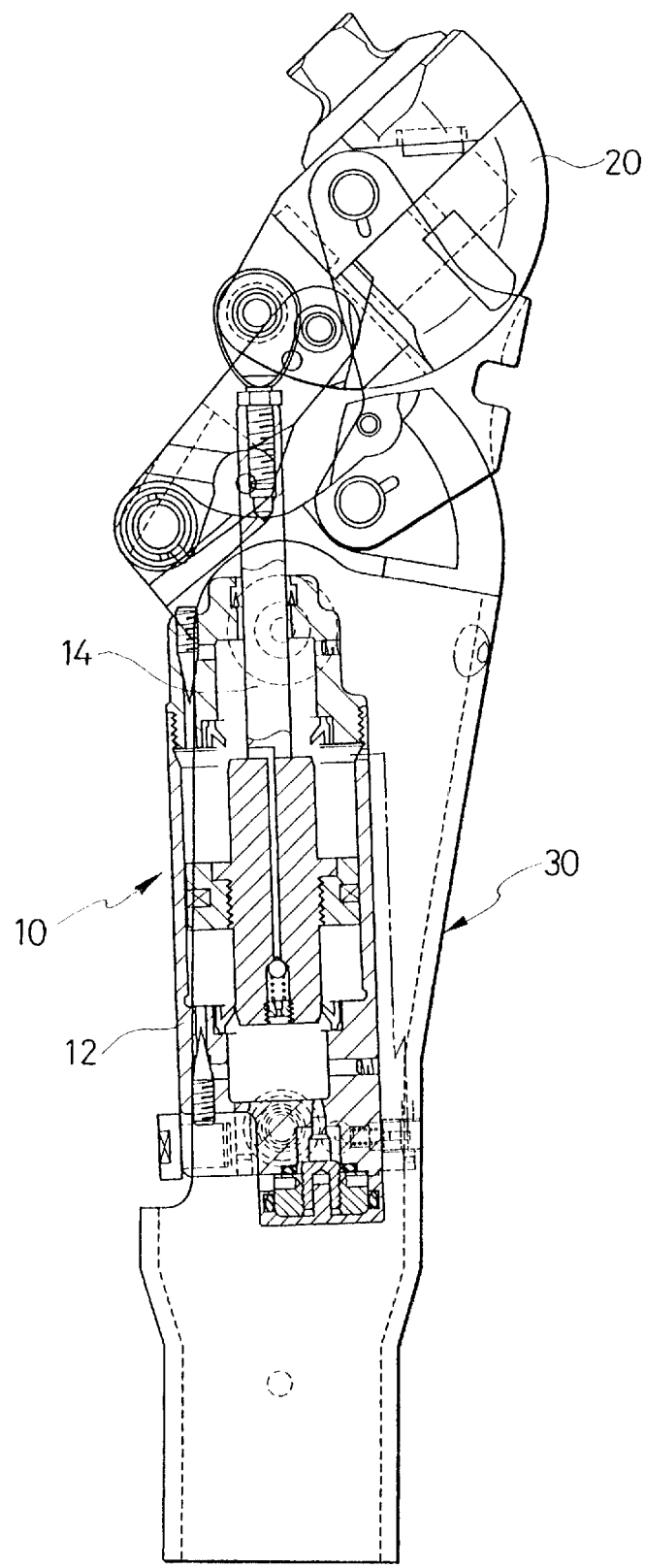
FIG. 2 is a view showing a state in which the knee of FIG. 1 is slightly bent.
Figure 3:
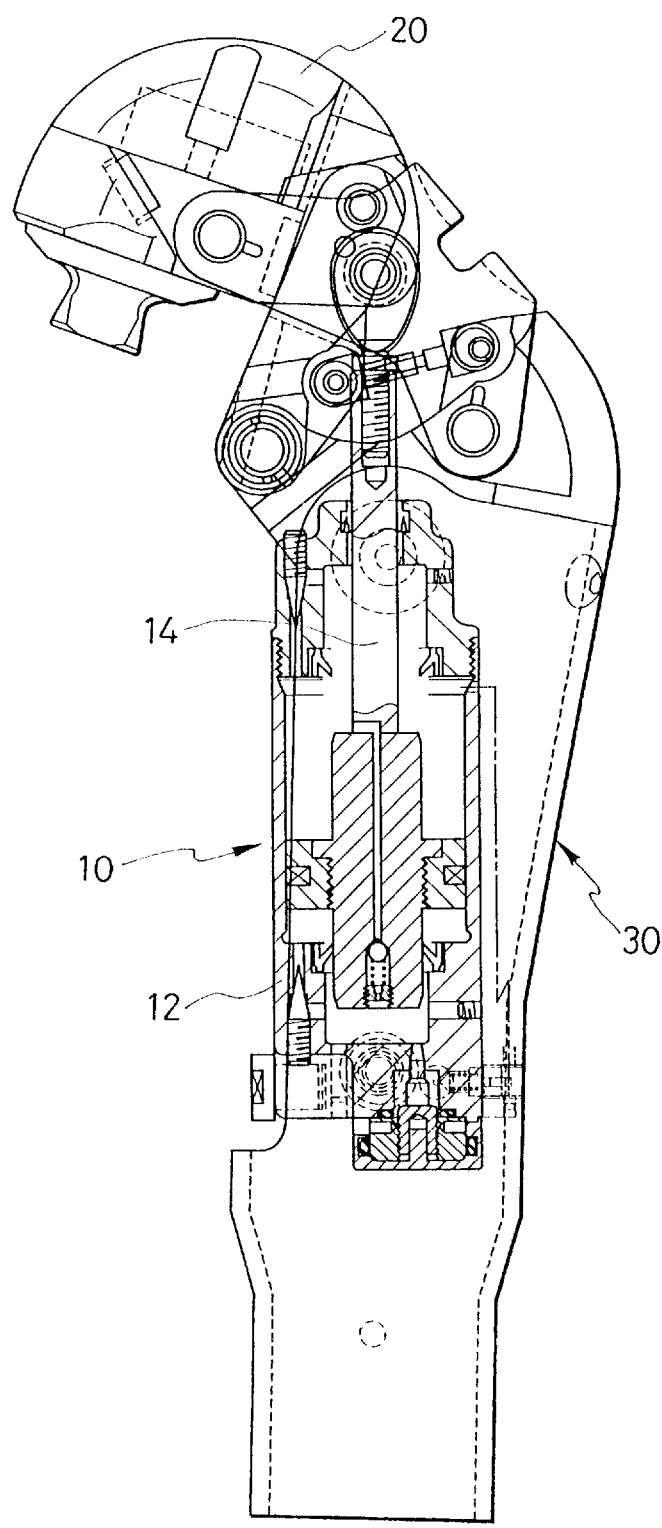
FIG. 3 is a view showing a state in which the knee of FIG. 1 is bent to the maximum extent.
Figure 4:
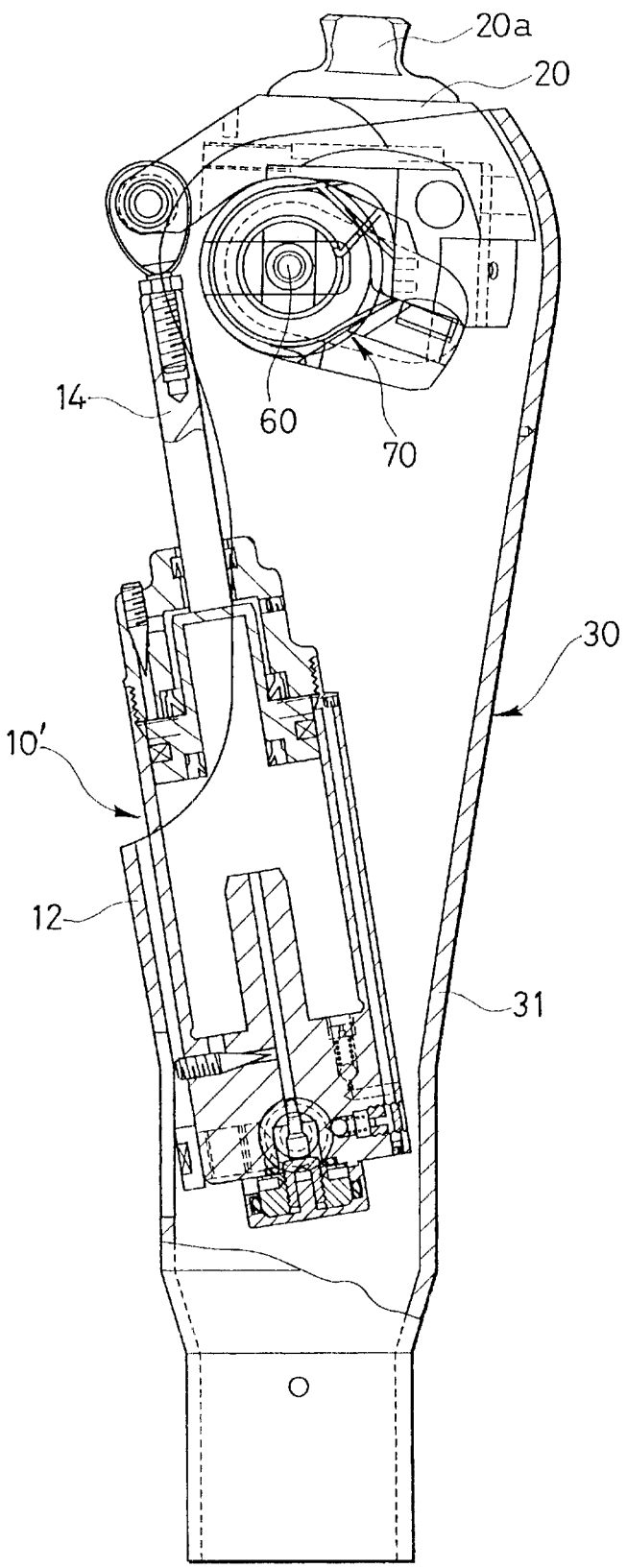
FIG. 4 is a view showing one form in which the present invention is applied to a prosthetic limb having a single-axis knee joint and a view showing a state in which the knee is fully stretched.
Figure 5:
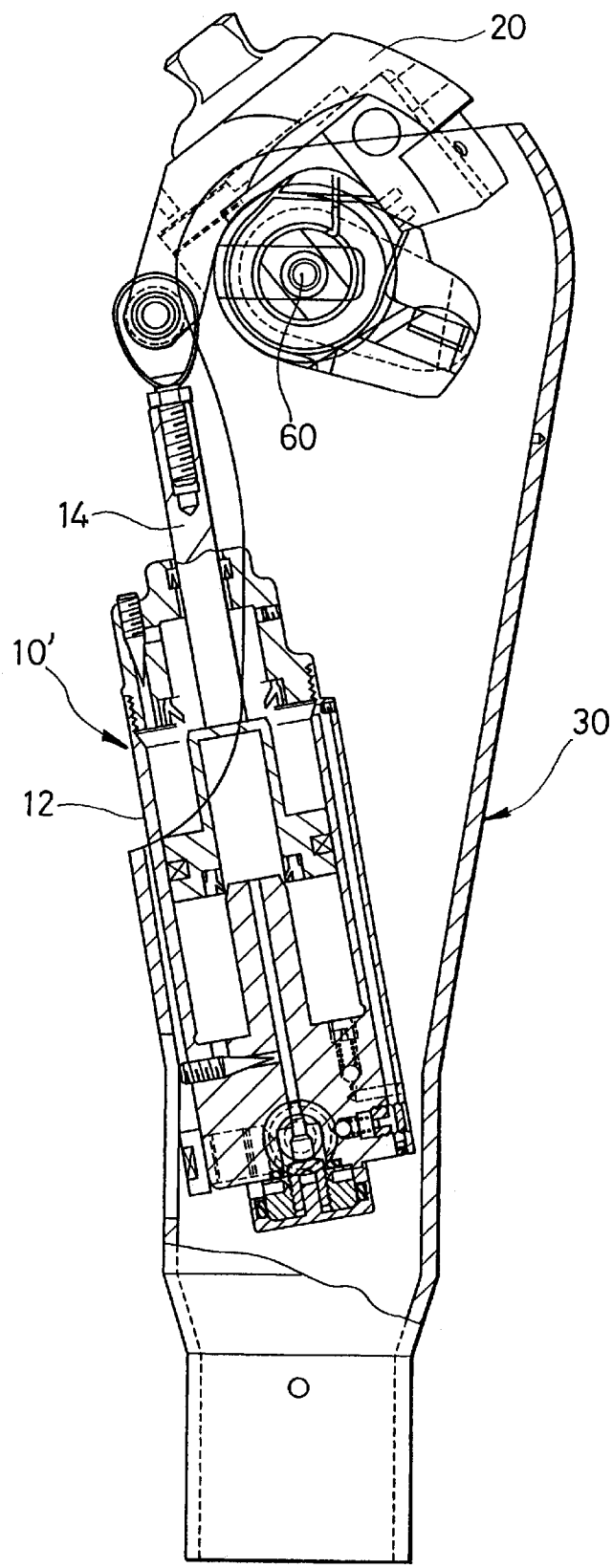
FIG. 5 is a view showing a state in which the knee of FIG. 4 is slightly bent.
Figure 6:
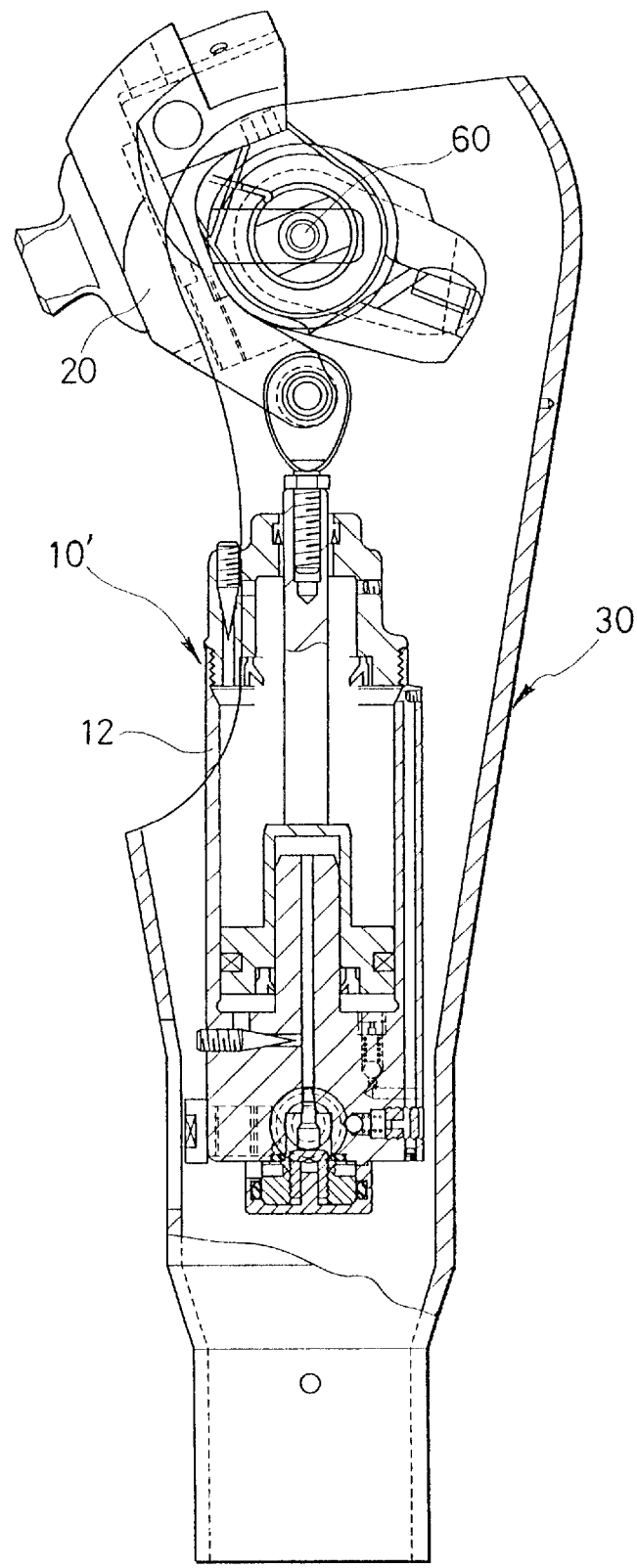
FIG. 6 is a view showing a state in which the knee of FIG. 4 is bent to the maximum extent.

The illustrated prosthetic limb is a femoral prosthetic limb for a person having no knee. FIGS. 1 to 3 show a prosthetic limb with a multi-axis knee joint and FIGS. 4 to 6 show a prosthetic limb with a single-axis knee joint. In those Figures, FIGS. 1 and 4 show a state in which the knee is stretched and thus the bending angle is zero, FIGS. 2 and 5 show a state in which the knee is slightly bent, and FIGS. 3 and 6 show a state in which the knee is bent to the maximum extent. Air-cylinder apparatuses 10, 10' of the present invention can be applied to a prosthetic limb with a multi-axis knee joint and also to a prosthetic limb with a single-axis knee joint. Although the air-cylinder apparatuses 10, 10' of the present invention are assigned with reference numerals 10, 10' only for the sake of convenience of explanation, first to fourth embodiments as later described can be applied as those air-cylinder apparatuses. The multi-axis knee joint is difficult to be applied to an air-cylinder apparatus having a long stroke because it includes a link mechanism and therefore, there is no spatial allowance at the knee joint area. In contrast, the single-axis knee joint has a comparatively large spatial allowance at the knee joint area when compared with the multi-axis knee joint although there is provided a load-brake around the single-axis, and therefore, it can effectively be applied to an air-cylinder apparatus having a long stroke, too.

Any of the above prosthetic limbs is provided at an upper part thereof with a femoral member 20 which is made of aluminum alloy. The femoral member 20 is in the form of a knee and integrally includes a connecting portion 20a for connecting a socket, not shown, to a part thereof. The socket receives therein an amputated end of the limb of a person who wears the prosthetic limb and transmits a load of the wearer to the femoral member 20. At a lower part of the femoral member 20, there is a crus member 30. A chief member composing the crus member 30 is a frame 31 having a hollow interior and extending towards the foot part from the knee part. The crus member 30 and the femoral member 20 can be bent and stretched by the knee joint. The multi-axis knee joint shown in FIGS. 1 to 3 includes a front link 40 located on a front side of the knee and a rear link 50 located on a rear side of the knee. The front and rear links 40, 50 extend in an up and down direction when the knee is in a stretched state and their upper end parts 40a, 50a are rotatably connected to the femoral member 20. Lower end parts 40b, 50b of the front and rear links 40, 50 are rotatably connected to the crus member 30. By this, the femoral member 20, the front link 40, the rear link 50 and the crus member 30 constitute a constrained chain capable of making only a constant motion. On the other hand, in the prosthetic limb having a single-axis knee joint shown in FIGS. 4 to 6, the femoral member 20 and the crus member 30 are rotatably connected together by a knee pin 60 disposed at the knee part. Around the knee pin 60, there is provided a load brake 70 for generating a braking force in response to the load of the wearer applied thereto. The load brake 70 is of the same known type as disclosed in U.S. Pat. No. 3,863,274 (corresponding to Japanese Patent Publication No. S52-46432), in which in response to the load of the wearer applied thereto, a through-hole formed in a brake block is reduced in diameter, thereby generating a braking force.

In contrast to the prosthetic limb thus constructed, the air-cylinder apparatuses 10, 10' are each supported at a cylinder bottom of the cylinder body 12 by a frame 31 through pin connection and are each rotatably connected at one end portion of a piston rod 14 extending outward from the cylinder head of the cylinder body 12 to the femoral member 20. The air-cylinders 10, 10' are each kept in the hollow frame 31 irrespective of the bending degree of the knee. The air-cylinders 10, 10' assist the bending and stretch-ing motion of the knee so that the wearer of the prosthetic limb can walk in a natural attitude. As the assisting functions of the air-cylinder apparatuses 10, 10', there are a first function for applying a resisting force against the bending motion of the knee at the bending time of the knee, a second function for swinging out the crus member forward with an accelerating speed after the knee is bent, and a third function for applying a cushioning force at a final stage of the stretching motion. According to this invention, the first and second functions, in particular, of the air-cylinder apparatuses 10, 10' can be optimized in accordance with the walking speed.

First Embodiment

Figure 7:
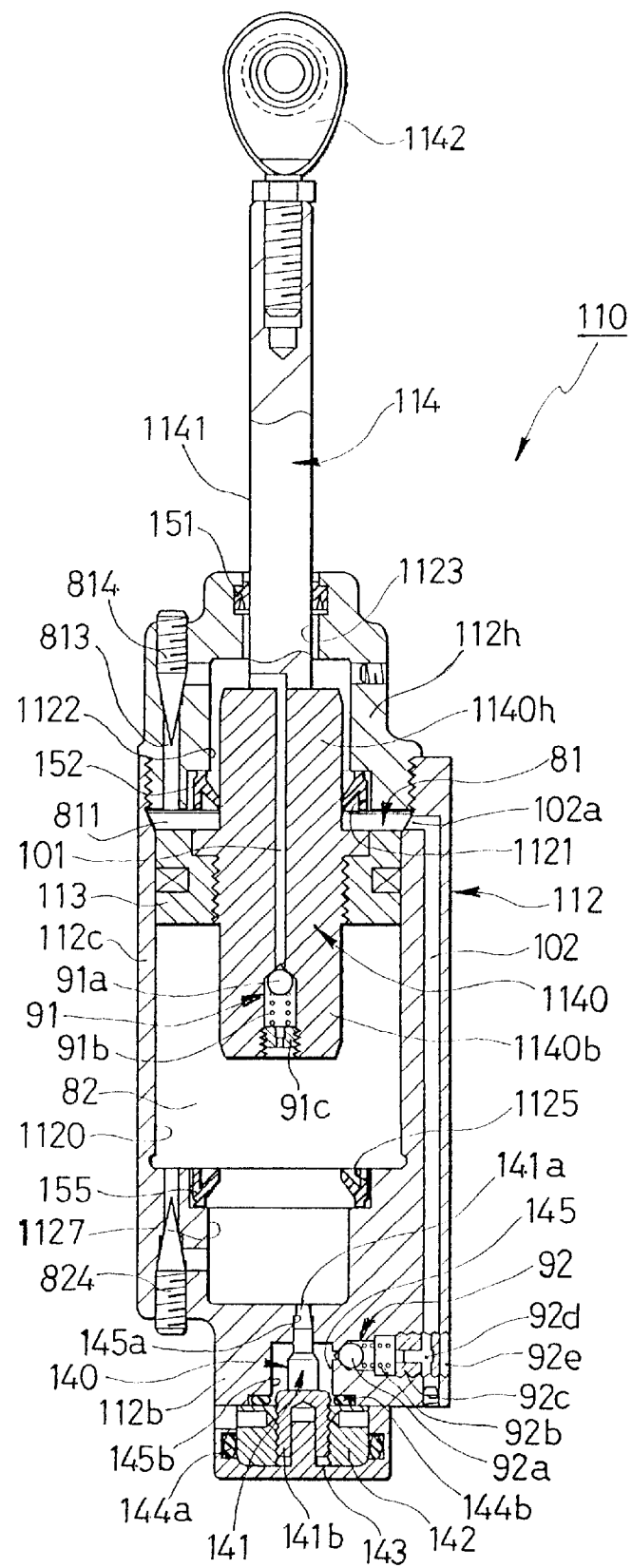
FIG. 7 is a view showing a first embodiment of the present invention and a sectional view showing a state in which the knee is fully stretched.
Figure 8:
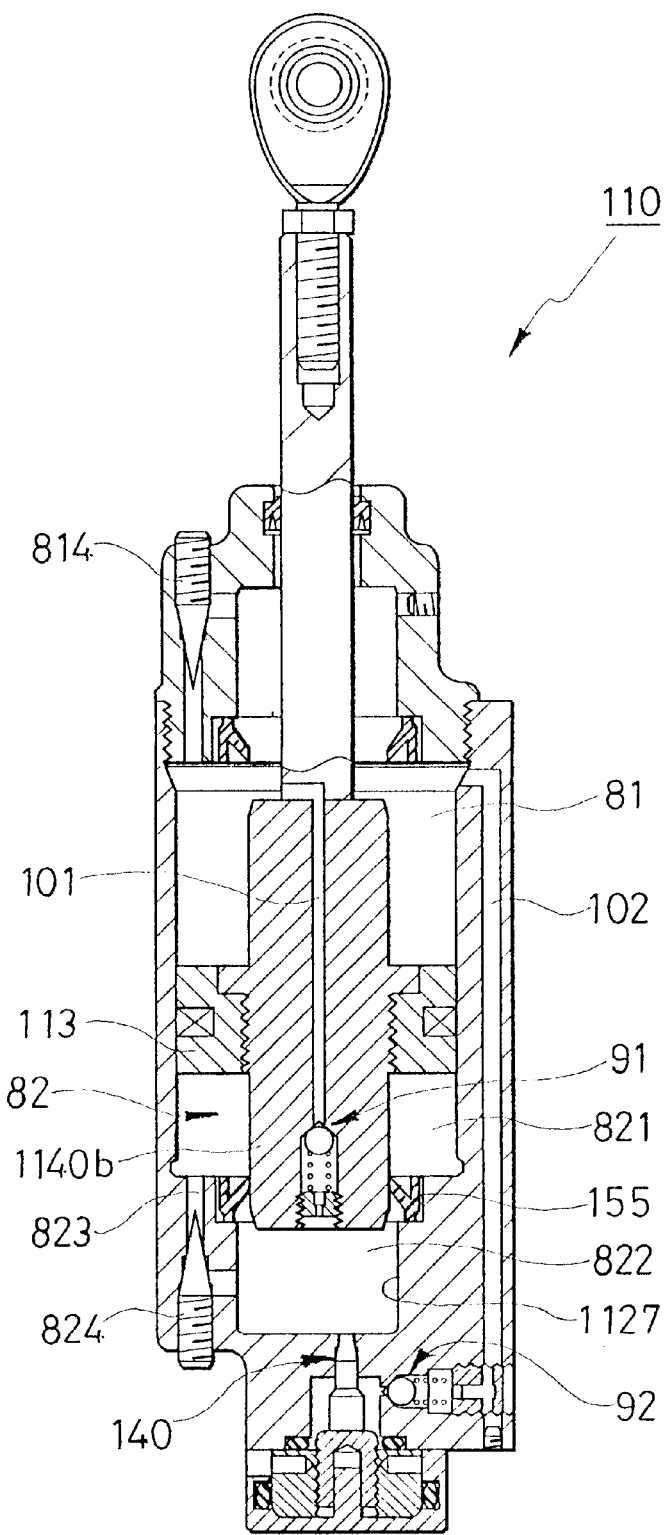
FIG. 8 is a view showing a state in which the knee of FIG. 7 is slightly bent.
Figure 9:
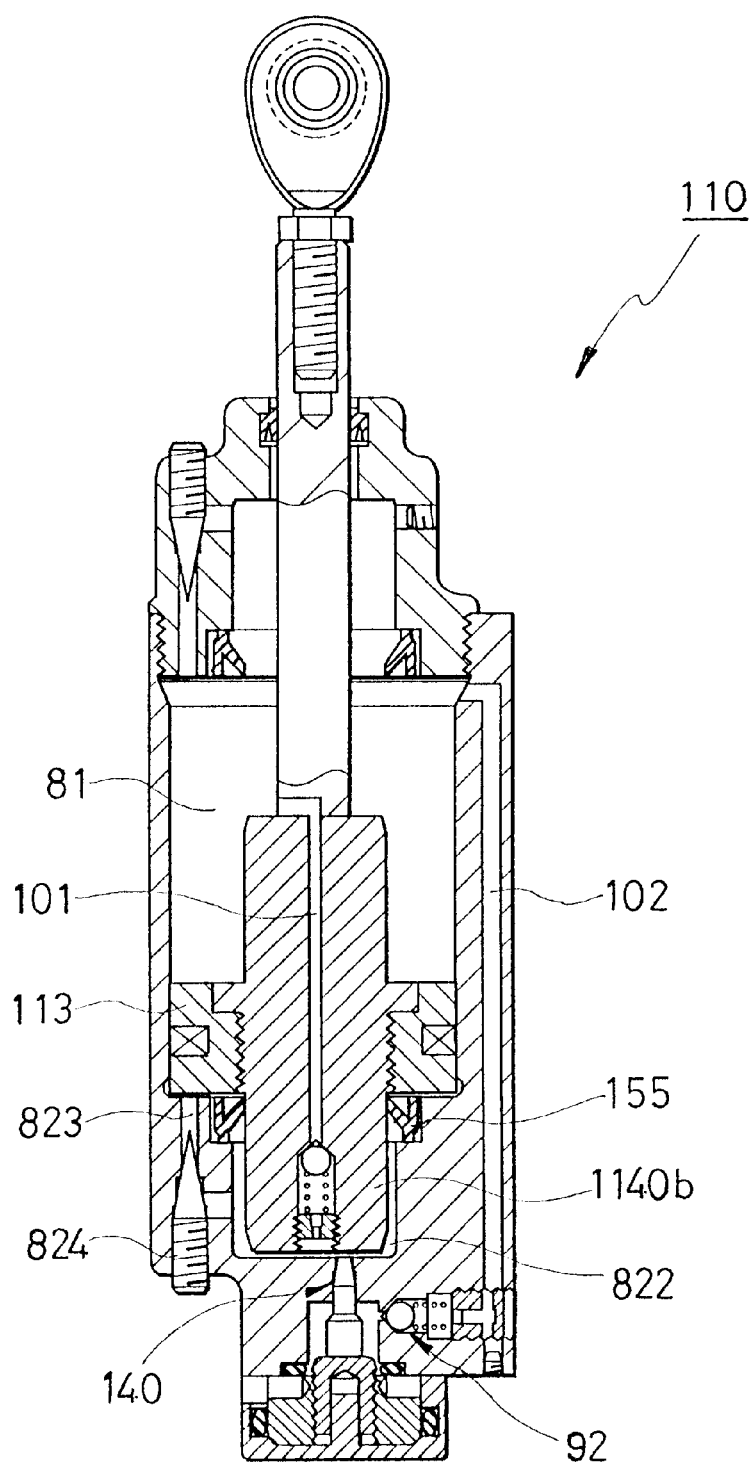
FIG. 9 is a view showing a state in which the knee of FIG. 7 is bent to the maximum extent.

FIGS. 7 to 9 show an air-cylinder apparatus 110 according to a first embodiment of the present invention. Each of those Figures is corresponding one of FIGS. 1 to 3 or FIGS. 4 to 6. FIG. 7 shows a state in which the knee is fully stretched and the bending angle is zero, FIG. 8 shows a state in which the knee is slightly bent, and FIG. 9 shows a state in which the knee is bent to the maximum extent. All other embodiments to be described later are also shown in those three states.

The air-cylinder apparatus 110 comprises a cylindrical cylinder body 112 which is made of aluminum alloy or synthetic resin. The cylinder body 112 includes a cylinder tube 112c having a uniform inside diameter, a head part 112h located at one end of the cylinder tube 112c and adapted to close this end, and a bottom part 112b located at the other end of the cylinder body 112c and adapted to close this end. In order to set up parts, such as a piston, within the cylinder body 112, at least one of the head part 112h and the bottom part 112b (in general, head part 112h) can be removed from the cylinder tube 112c. Normally, the head part 112h is threadingly engaged with the cylinder tube 112c.

The interior of the cylinder body 112 is divided, by the piston 113, into a first chamber 81 located on the head side and a second chamber 82 located on the bottom side. The piston 113 is fitted into the cylinder tube 112c for movement in the axial direction. The piston 113 is integrally supported by the piston rod 114. The piston rod 114 integral with the piston 113 comprises an enlarged-diameter section 1140 for supporting the piston 113, and a reduced-diameter section 1141 extending from one end of the enlarged-diameter section 1140 and a reduced-diameter rod part 1141 extending through the head part 112h. The reduced-diameter rod part 1141 extending outward from the head part 112h of the cylinder body 112 is provided at an external end thereof with a lug 1142 for connecting the reduced-diameter rod part 1141 to the femoral member of the prosthetic limb. The enlarged-diameter section 1140 extends through the piston 113 projects forward and backward therefrom. The enlarged-diameter section 1140 includes two projections 1140h, 1140b projecting, respectively, towards the head side and the bottom side from the piston 113. Those projections 1140h, 1140b are equal in outside diameter and generally equal in height.

Next, attention should be paid to the head part 112h and the bottom part 112b of the cylinder body 112. The head part 112h has three holes each having a different diameter from others and arranged in an axial direction thereof. The first hole is an enlarged-diameter hole 1121 located at an opening portion confronting an internal hole 1120 of the cylinder tube 112c. The second hole, which is adjacent to the enlarged-diameter hole 1121, is a middle sized-diameter hole 1122 which is smaller in diameter than the enlarged-diameter hole 1121 and which forms a step part between the enlarged-diameter hole 1121 and itself. The third hole arranged next to the middle sized-diameter hole 1122 is a reduced-diameter hole 1123 which is open externally. Those three holes 1123, 1122 and 1121, as a whole, forms a through-hole having a co-axis and extending through the head part 112h.

There is provided, at the reduced-diameter hole 1123, a first seal member 151 for sealing an outer periphery of the reduced-diameter hole 1141 of the piston rod 114. There is provided, on the step part between the middle sized-hole 1122 and the enlarged-diameter hole 1121, a second seal member 152 for sealing an outer periphery of the projection 1140h of the piston rod 114. By sealing the outer periphery of the projection 1140h which is brought into the middle sized-hole 1122 at a final stage of the stretching motion of the knee, the second seal member 152 causes a chamber 811 round the projection 1140h proximate to the piston 113 to function as a cushion chamber. The air in the cushion chamber 811 flows towards the second chamber 82 only through a throttle passage 813 formed in the head part 112h. At the throttle passage 813, there is provided a cushion adjustment screw 814 through which the throttling degree can be adjusted from outside. In order to permit the flow of air from the first chamber 81 towards the second chamber 82, there is provided a first passage 101 including a first check valve 91 within the piston rod 114. The first passage 101 extends through the center of the enlarged-diameter section 1140 of the piston rod 114. One end of the first passage 101 is open into the second chamber 82 from an end face of the section 1140 and the other end radially traverses the reduced-diameter rod section 1141 and is open in the vicinity of the other end face of the enlarged-diameter section 1140. The first check valve 91 includes, as a matter of course, a ball 91a as a valve body, and a valve spring 91b for exerting a closing force to the ball 91a, and a spring member 91c for supporting one end of the valve spring 91b. The constitution relating to the cushion chamber 811 is same as that disclosed by the aforementioned U.S. Pat. No. 5,405,407.

In contrast to the first passage 101 for permitting the flow of air from the first chamber 81 towards the second chamber 82, there is also provided another passage for permitting the reversed flow of air, namely, from the second chamber 82 towards the first chamber 81. This second passage 102 is arranged at the cylinder body 112 in contrast to the first passage 101 being arranged at the piston rod 114. The second passage 102 extends through the interior of a side wall of the cylinder tube 112c, which is partly thick in wall, from the head side towards the bottom side in parallel to the axis of the cylinder body 112. The second passage 102 is, on the head side, in communication with the first chamber 81 via an opening 102a near the end face of the head part 112h and is, on the bottom side, in communication with the second chamber 82 via a check valve 92 and a constant throttle valve 140 received in the bottom part 112b.

The second check valve 92 for the second passage 102 is disposed within a hole orthogonal to the second passage 102. The second check valve 92 includes, as in the case with the first check valve 91, a ball 92a as a valve body, a valve spring 92b for exerting a closing force to the ball 92a, and a screw member 92c for supporting one end of the valve spring 92b. The screw member 92c includes therein a hole 92d having a T-shaped configuration in section, this hole 92d being provided for obtaining the function as a passage, and at a head part confronting outside a driver groove 92e, this driver groove 92e being provided for setting up the second check valve 92. On the other hand, the constant throttle valve 140 is connected, in serial relation, to the second check valve 92 on the second passage 102. The constant throttle valve 140 is located within a step hole 145 disposed at a lower part of the bottom part 112b of the cylinder body 112. The step hole 145 comprises a reduced-diameter hole 145a including a valve seat, and an enlarged-diameter hole 145b which is enlarged in diameter compared with the hole 145a. A side part of the enlarged-diameter hole 145b is in communication therein with a hole containing the second check valve 92, while one end of the reduced-diameter hole 145a is defined as an opening which is communicated with the second chamber 82 formed within the cylinder body 112. The constant throttle valve 140 comprises a valve body 141 which is provided at one end thereof with a tapered part 141a and at the other end with a sleeve-like guide part 141b, a threaded ring 142 threadingly engageable with an outer periphery of the guide part 141b of the valve body 141, a cap 143 engaged with the guide part 141b of the valve body 141 and covering an external side of threaded ring 142, and O-rings 144a, 144b for sealing joining surfaces of between the cap 143 and the threaded rig 142 and between the threaded ring 142 and the bottom part 112b, respectively. By converting a rotary motion to a linear motion utilizing the threading engagement between the threaded ring 142 and the guide part 141b of the valve body 141, the constant throttle valve 140 can adjust the throttling degree and opening degree of the valve body 141. Since the constant throttle valve 140 is disposed on the second passage 102 and its valve body 141 is confronted with the opening leading to the second chamber 82, the flow of air from the second chamber 82 towards the first chamber 81 is normally restricted. An opening area of the constant throttle valve 140 is set, for example, 0.008 to 0.009 mm$^2$.

In the air-cylinder apparatus 110 according to the first embodiment of the present invention, an internal structure of the second chamber 82 facing the constant throttle valve 140 is same as the first chamber 81. At the bottom part 112b, there are provided two holes each having a different diameter along an axial direction of the bottom part 112b, which holes are adjacent to and in communication with the internal hole 1120 of the cylinder tube 112c. The first hole is an enlarged-diameter hole 1125 located at the opening confronting the internal hole 1120 of the cylinder tube 112c. The second hole adjacent to the enlarged-diameter hole 1125 is a middle sized-hole 1127 which is smaller in diameter than the enlarged-diameter hole 1125 and which forms a step part between the enlarged-diameter hole 1125 and itself. The middle sized-diameter hole 1127 and the enlarged-diameter hole 1125 are coaxial with the internal hole 1120 of the cylinder tube 112c. On the step part between the middle sized-diameter hole 1127 and the enlarged-diameter hole 1125, there is provided a lip type seal member 155 for sealing the outer periphery of the projection 1140b of the piston rod 114. The seal member 155 is adapted to seal the outer periphery of the projection 1140b of the enlarged-diameter section 1140 at a stage where the bending angle of the knee exceeds a predetermined value. The time point for the seal member 155 to seal the outer periphery of the projection 1140b is the time when the bending degree of the knee is increased to bring the projection 1140b into the middle sized-hole 1127 as a recess. That time point corresponds to the stage where the bending angle of the knee exceeds 50 degrees (this angle is the maximum bending angle in a normal walking speed). Such a time point as just mentioned above can easily be set by changing either the length of the projection 1140b of the enlarged-diameter section 1140 or the location where the seal member 155 is arranged.

Figure 10:
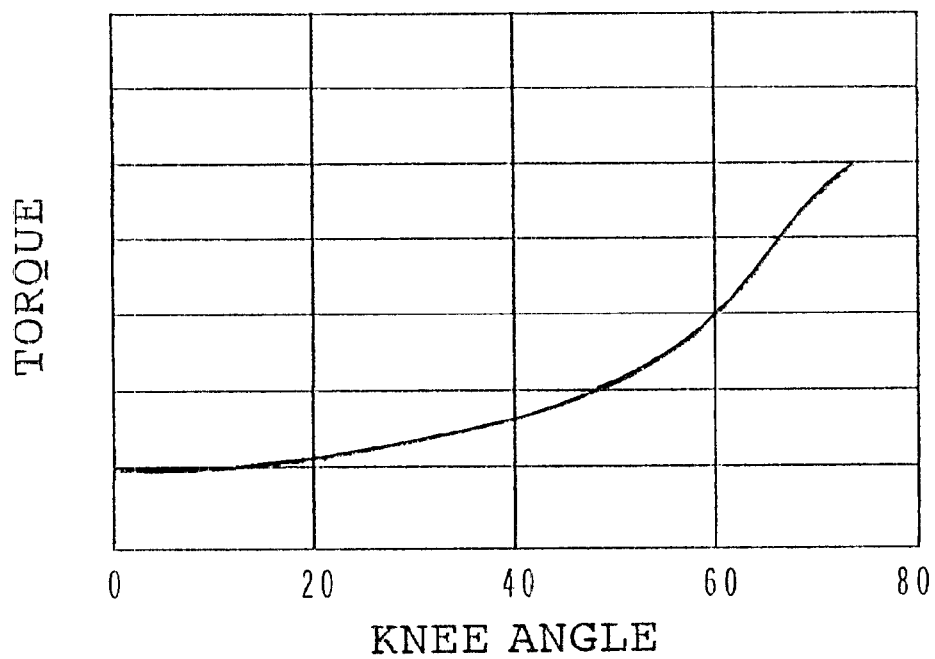
FIG. 10 is a graph showing pressure characteristics of the first embodiment.

From a different viewpoint, to seal the outer periphery of the projection 1140*b* by the seal member 155 is to divide the second chamber 82 on the bottom side into two chambers. One of the divided chambers is a chamber 821 located within the cylinder tube 112*c* and defined by the piston 113 and the seal member 155. The other is a chamber 822 which is defined within the middle sized-diameter hole 1127. There is provided at a bottom part of the middle sized-diameter hole 1127 an opening which is in communication with the constant throttle valve 140. The chamber 822 is a predetermined chamber confronting the opening leading for communication to the constant throttle valve 140. At the bottom part 112*b*, there is provided a throttle passage 823 as an auxiliary passage for communicating with the two chambers 821, 822. The throttle passage 823 is open to the chamber 821 at a location more radially outside than the seal member 155. At a midway of the throttle passage 823, there is provided a screw type needle valve 824 as a throttle valve. An opening area of the throttle valve 824 is small compared with that of the constant throttle valve 140. For example, the opening area of the throttle valve 824 is set 0.003 to 0.004 mm$^2$. At a stage where the bending degree of the knee is small and the second chamber 82 is not yet divided into two, the constant throttle valve 140 generates a torque necessary for increasing the pressure in the second chamber 82. On the other hand at a stage where the bending degree of the knee is increased and the second chamber 82 is divided into two, the constant throttle valve 140 increases the pressure in the chamber 822 and the throttle valve 824 increases the pressure in the chamber 821. FIG. 10 is a graph showing one example of pressure characteristics in the air-cylinder apparatus 110 in which the bending angle of the knee is plotted along the abscissa and the pressure generated in the second chamber 82 or torque attributable to the generation of the pressure is plotted along the ordinate. As shown in the characteristics chart of FIG. 10, the air-cylinder apparatus 110 exhibits very smooth characteristics.

Second Embodiment

Figure 11:
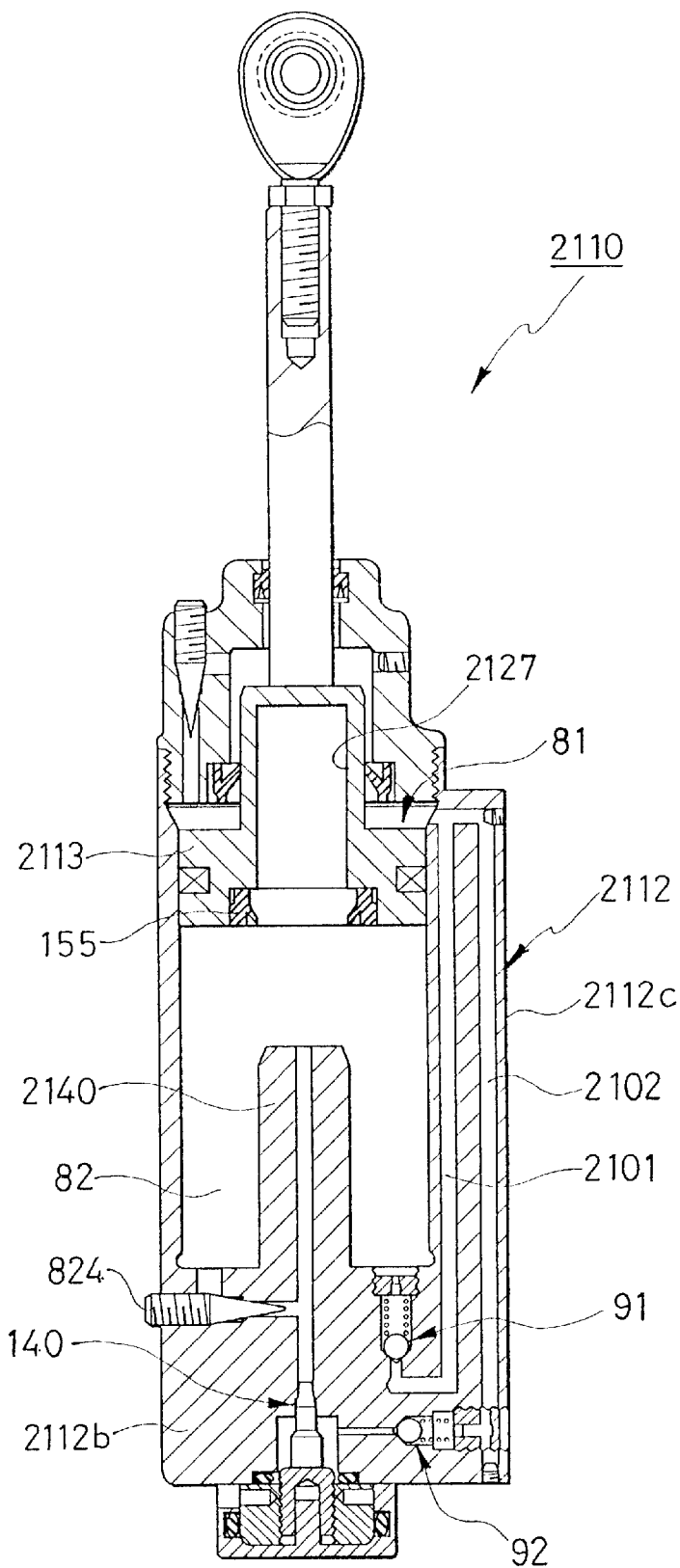
FIG. 11 is a view showing a second embodiment of the present invention and a sectional view showing a state in which the knee is fully stretched.
Figure 12:
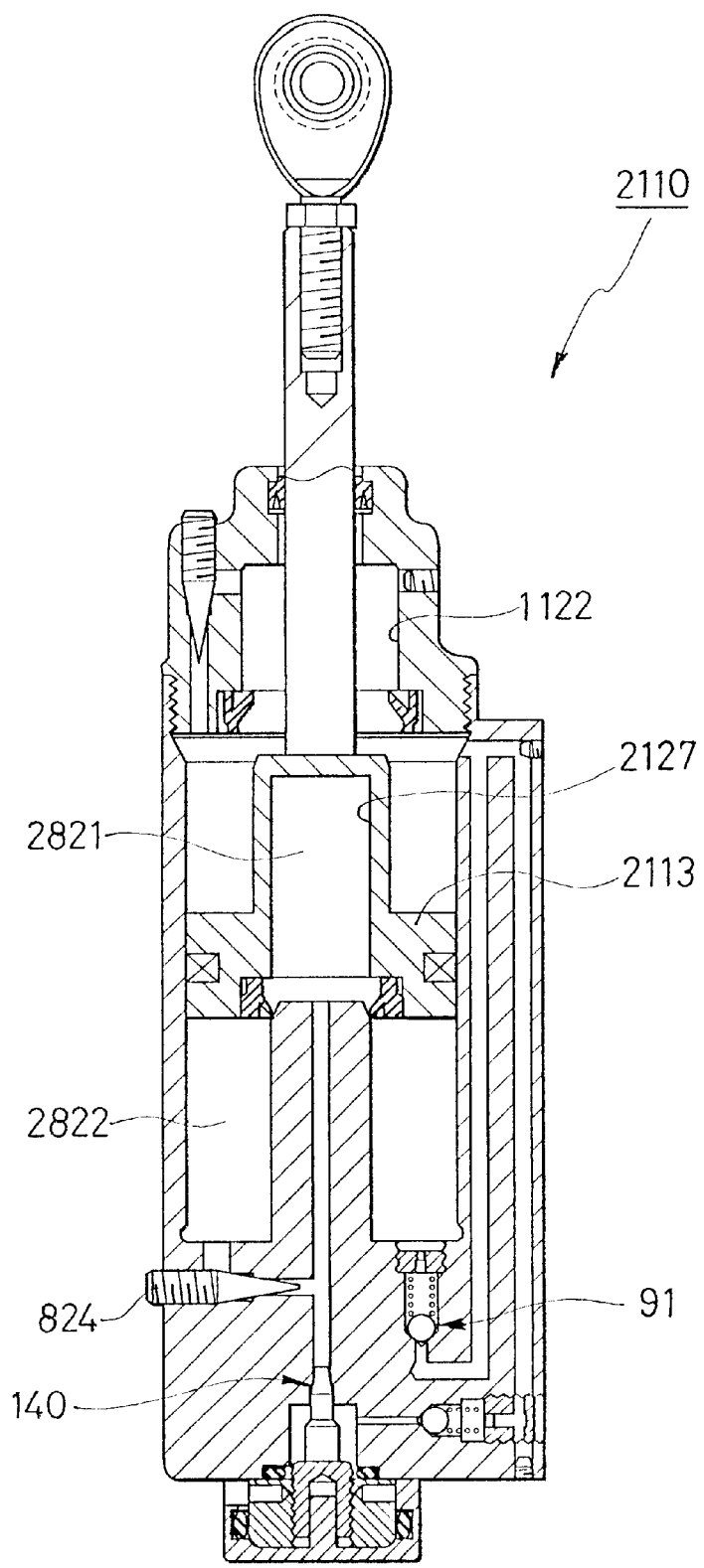
FIG. 12 is a view showing a state in which the knee of FIG. 11 is slightly bent.
Figure 13:
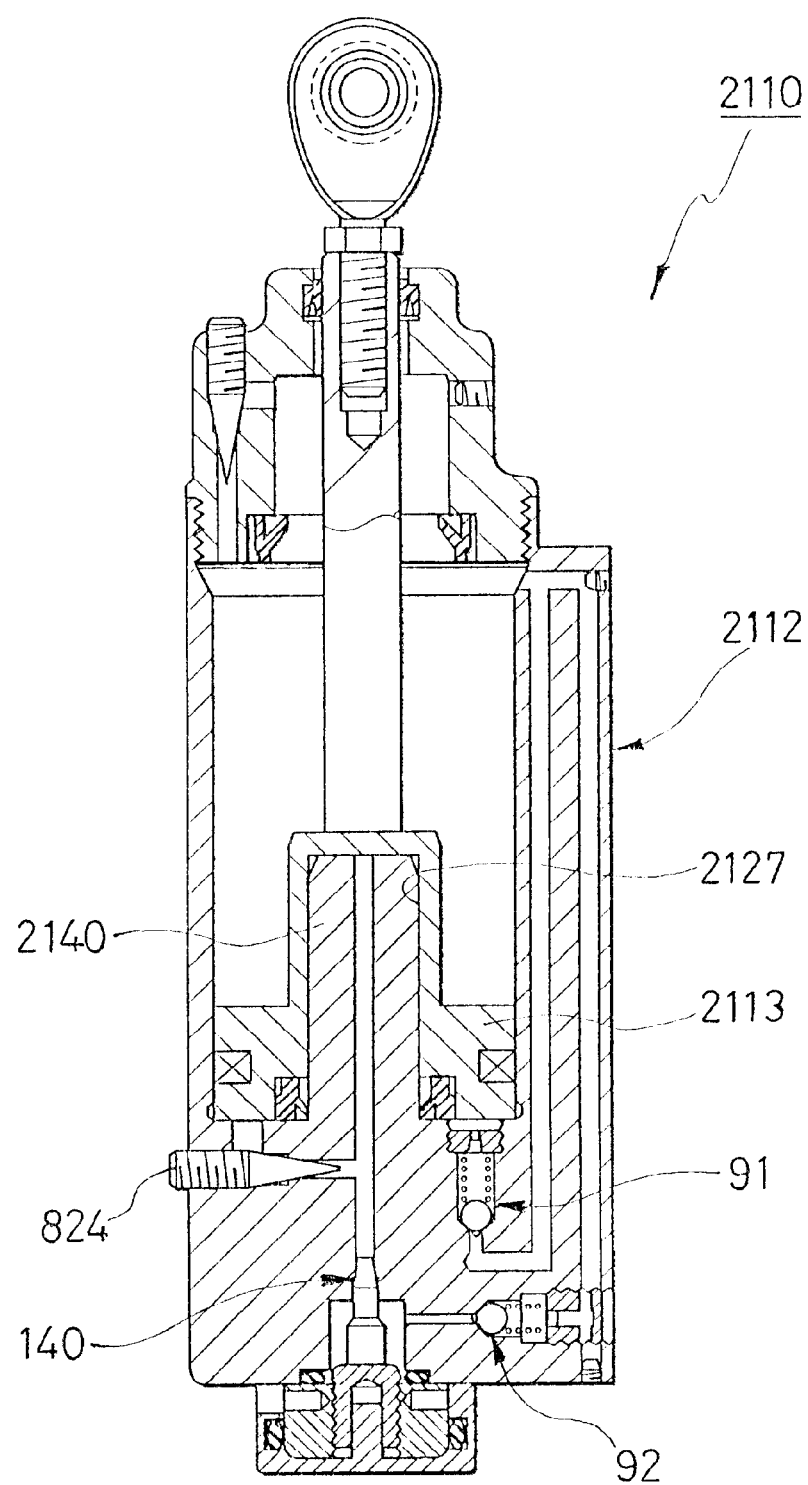
FIG. 13 is a view showing a state in which the knee of FIG. 11 is bent to the maximum extent.

FIGS. 11 to 13 show an air-cylinder apparatus 2110 according to a second embodiment of the present invention. In this air-cylinder apparatus 2110, a recess 2127 is provided at a piston 2113 of a cylinder body 2112, and a counterpart projection 2140 is provided at a bottom part 2112*b* of the cylinder body 2112. In accordance with this arrangement, a first passage 2101 including a first check valve 91 for permitting the flow of air from the first chamber 81 towards the second chamber 82 is, as in the case with a second passage 2102 as another communication passage, is disposed within a side wall of a cylinder tube 2112*c*. In the air-cylinder apparatus 2120 according to the second embodiment, the constant throttle valve 140, as in the case with the first embodiment, increases the pressure in the second chamber 82 at a stage where the bending angle of the knee is small. However, since the second chamber 82 is divided into two chambers 2821 and 2822 when the bending angle of the knee reaches a predetermined stage, the chamber 2821 is increased in pressure by the constant throttle valve 140 and the other chamber 2822 is increased in pressure by the throttle valve 824. The pressure characteristics thus obtained are same as FIG. 10. An additional feature of the air-cylinder apparatus 2110 is that the recess 2127 is concentrically formed in the piston 2123 which is moved into the middle sized-diameter hole 1122 on the head side. Owing to this feature, the cylinder stroke can be enlarged. Moreover, since the capacity or the newly defined chamber 2822 can be increased, more sufficient pressure increase can be obtained.

Third Embodiment

Figure 14:
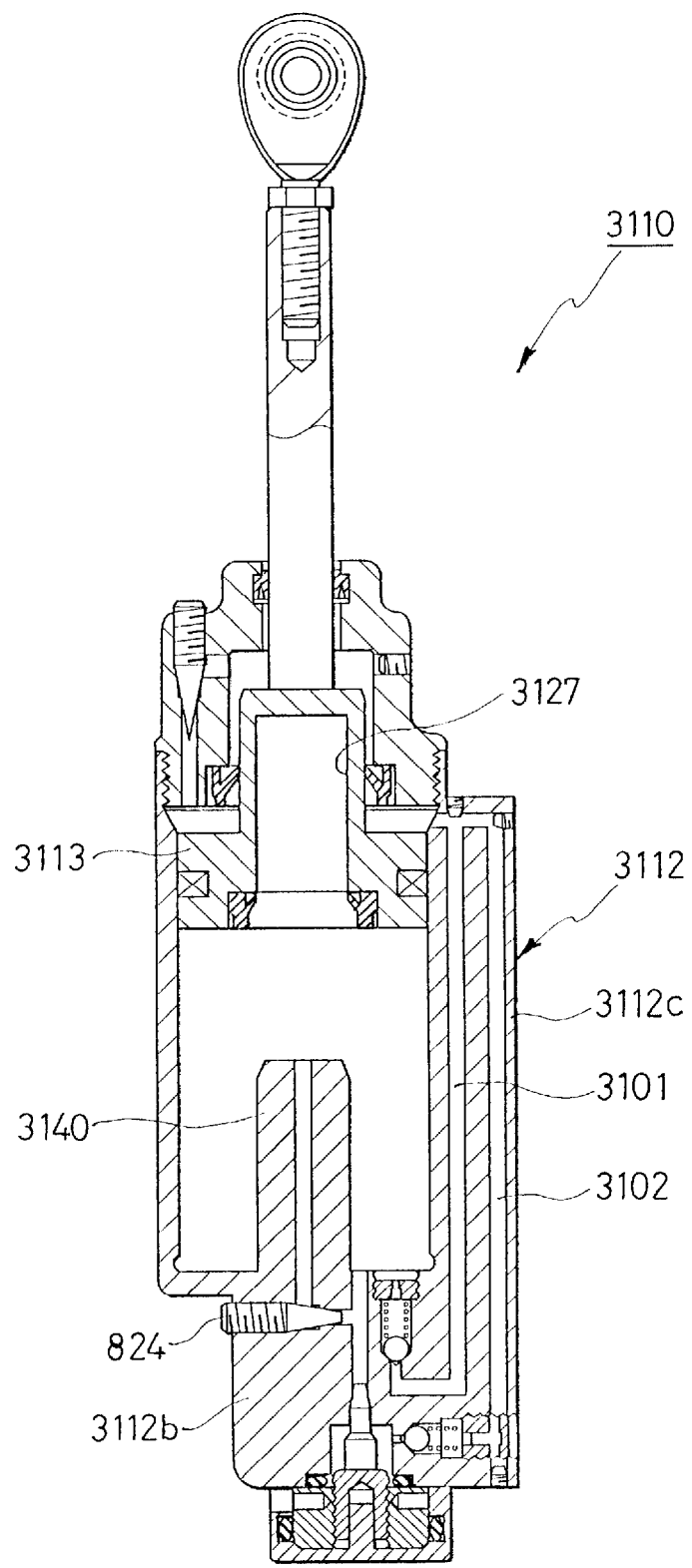
FIG. 14 is a view showing a third embodiment of the present invention and a sectional view showing a state in which the knee is fully stretched.
Figure 15:
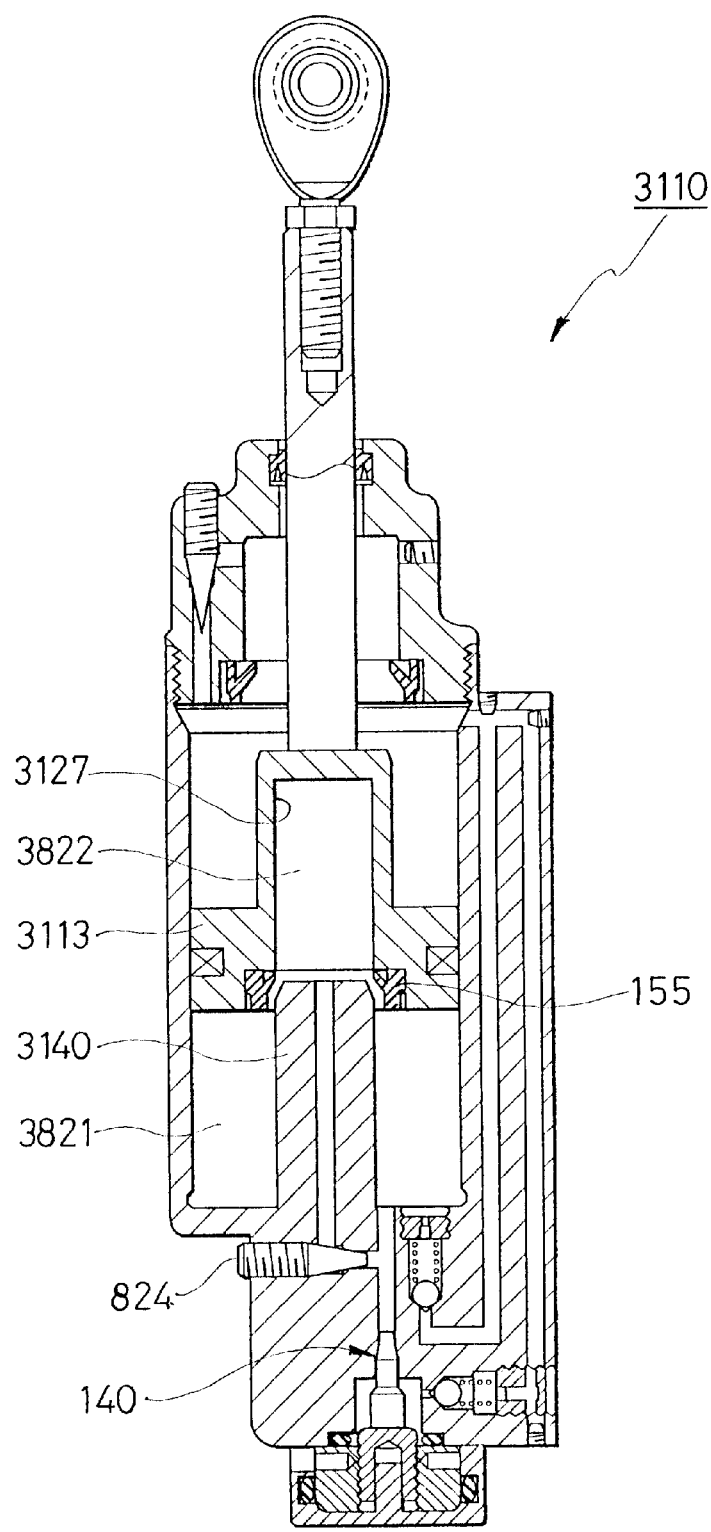
FIG. 15 is a view showing a state in which the knee of FIG. 14 is slightly bent.
Figure 16:
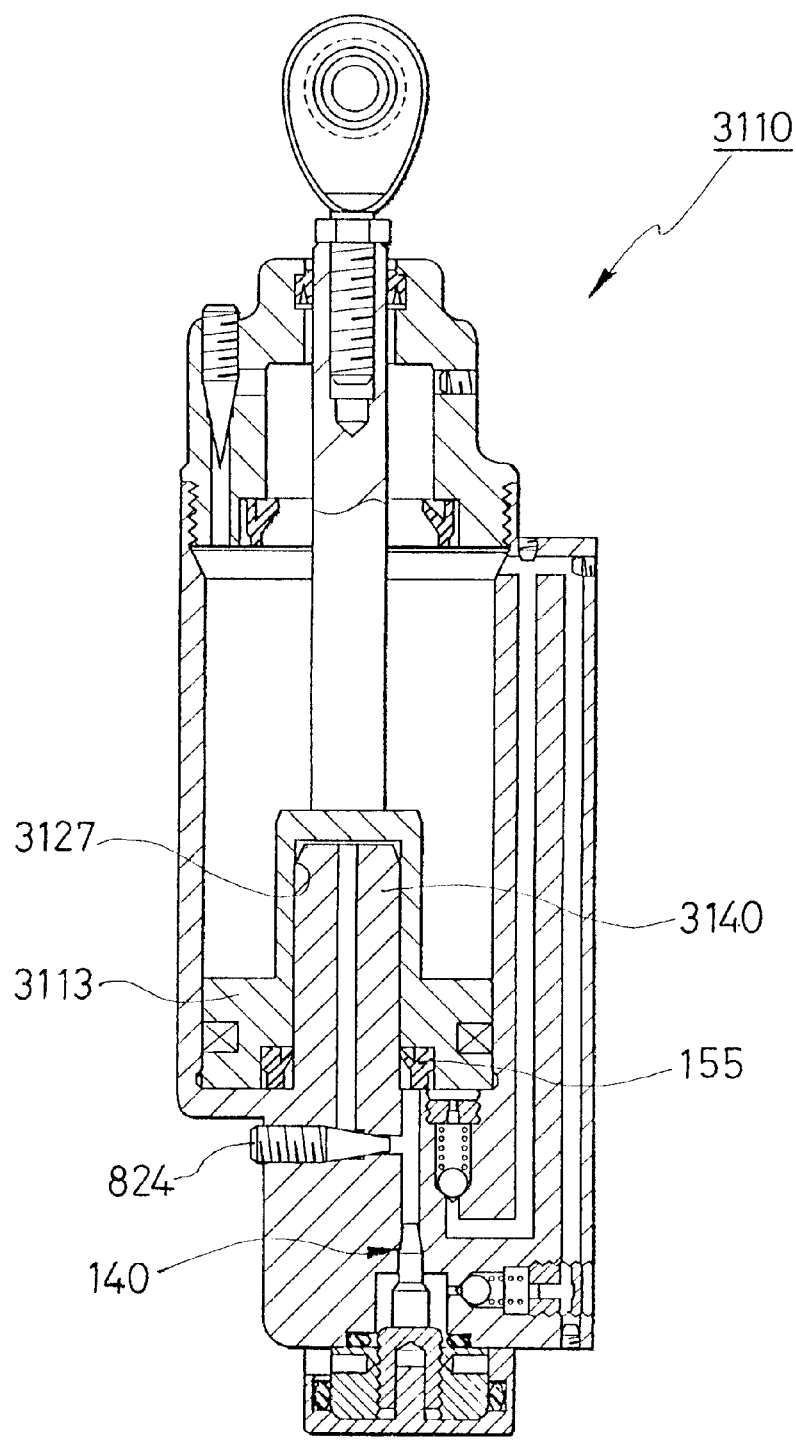
FIG. 16 is a view showing a state in which the knee of FIG. 14 is bent to the maximum extent.

FIGS. 14 to 16 show an air-cylinder apparatus 3110 according to a third embodiment of the present invention. This air-cylinder apparatus 3110 is common with the second embodiment in the respects that a recess 3127 formed in a piston 3113 is engaged with a projection 3140 formed on a bottom part 3112*b* of a cylinder body 3112 and a first passage 3101 and a second passage 3102 are disposed within a side wall of a cylinder tube 3112*c*. The third embodiment is different from the second embodiment in the following respects. The chambers defined as a result of division is reversed. A newly defined chamber 3822 is located within the recess 3127 of the piston 3113. Accordingly, the newly defined chamber 3822 is increased in pressure by the throttle valve 824 and a chamber 3821 at a side periphery of the projection 3140 is increased in pressure by the constant throttle valve 140. Since the newly defined chambers are reversed, the lip of the seal member 155 for sealing the outer periphery of the projection 3140 is revered in direction with respect to the second embodiment.

Fourth Embodiment

Figure 17:
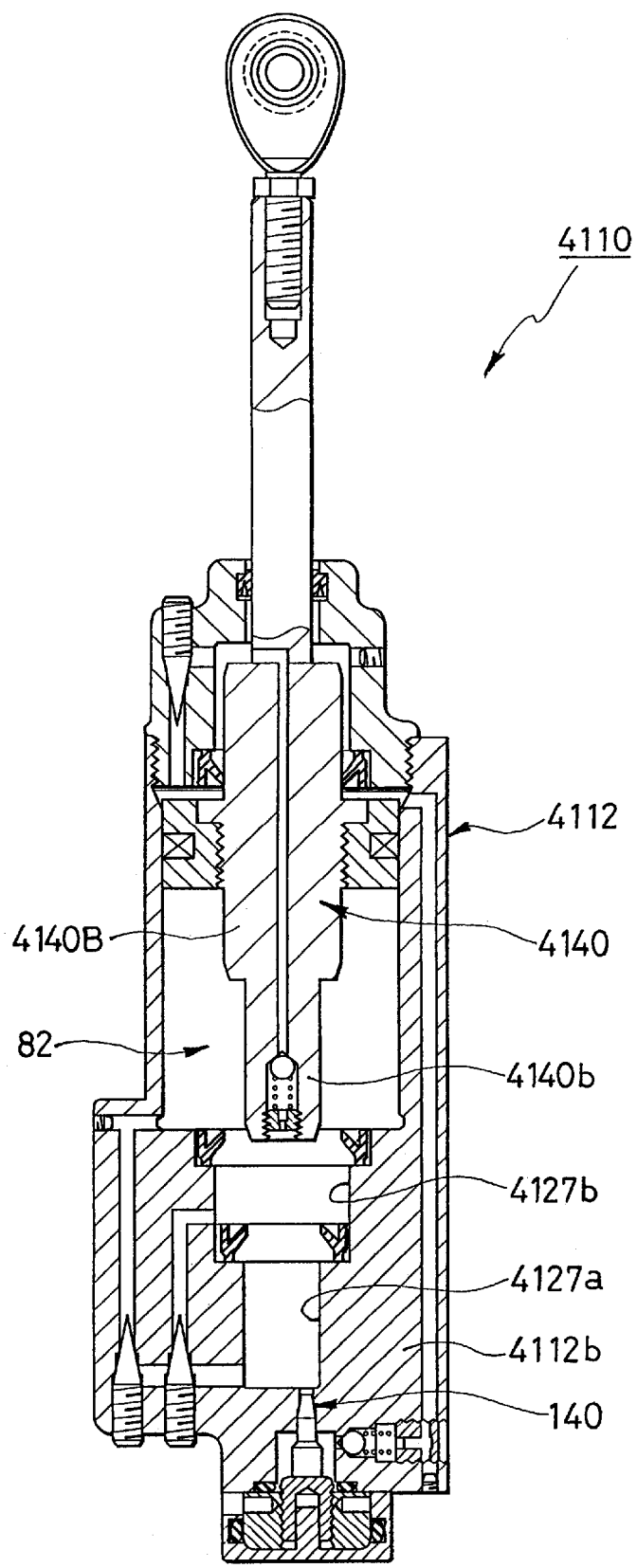
FIG. 17 is a view showing a fourth embodiment of the present invention and a sectional view showing a state in which the knee is fully stretched.
Figure 18:
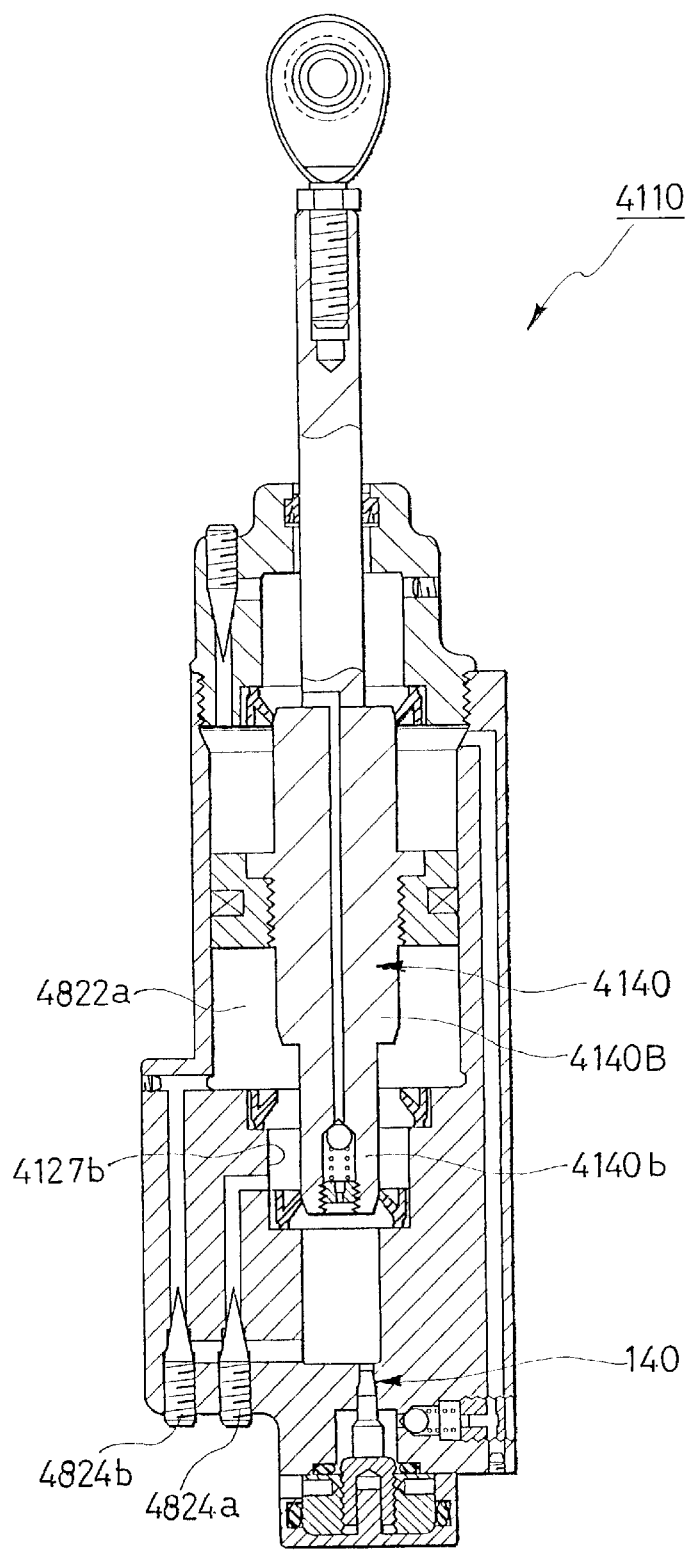
FIG. 18 is a view showing a state in which the knee of FIG. 17 is slightly bent.
Figure 19:
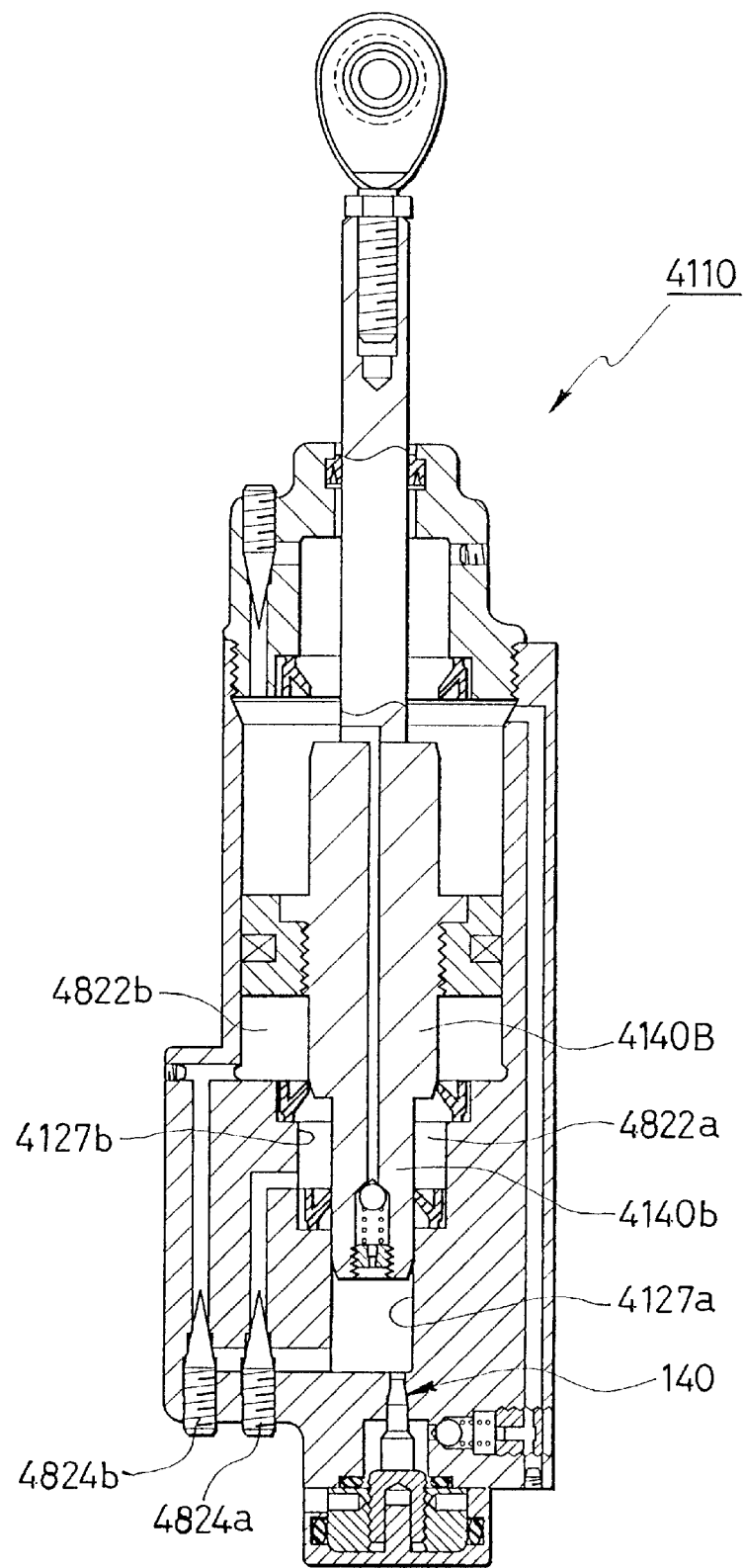
FIG. 19 is a view showing a state in which the knee of FIG. 17 is bent to the maximum extent.
Figure 20:
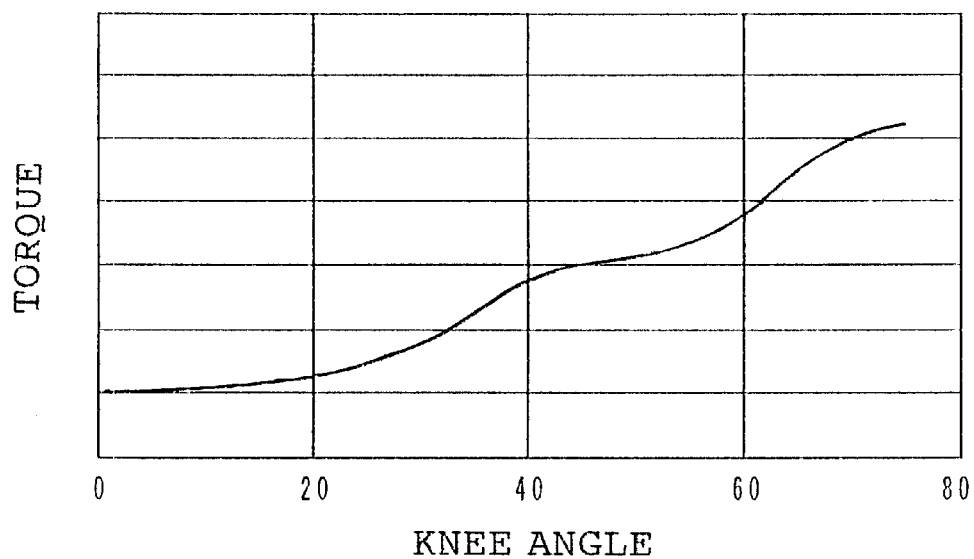
FIG. 20 is a graph showing pressure characteristics of the fourth embodiment.

FIGS. 17 to 19 show an air-cylinder apparatus 4110 according to fourth embodiment of the present invention. In this air-cylinder apparatus 4110, the throttling function is changed over three-stage. The basic idea of design is same as in the first embodiment. In order to make it possible to change the throttling function over three-stage, a projection extending towards the bottom side of an enlarged-diameter section 4140 consists of two portions, namely, a reduced-diameter portion 4140*b* and an enlarged-diameter portion 4140B. Hence, a reduced-diameter recess 4127*a* and an enlarged-diameter recess 4127*b* are formed in a bottom part 4112*b* of a cylinder body 4112. When the bending of the knee is progressed to some extent, first, the reduced-diameter projection 4140*b* is brought into the reduced-diameter recess 4127*a* and a new chamber 4822*a* is defined at the side periphery of the projection of the enlarged-diameter section 4140. When the bending degree of the knee is further increased, a new chamber 4822*b* is also defined at a side periphery of the enlarged-diameter projection 4140B. In an early stage of the bending motion of the knee, the constant throttle valve 140 takes the role for throttling with respect to the second chamber 82. However, with respect to the chambers 4822*a*, 4822*b* which are defined in a stage where the bending degree of the knee is increased, those throttle valves 4824*a*, 4824*b*, which are provided for the chambers 4822*a*, 4822*b*, respectively, take the role for throttling. The throttle valves 4824*a*, 4824*b* are set small in opening area compared with the constant throttle valve 140. However, the opening areas of the throttle valves 4824*a*, 4824*b* may be set equal to each other or different from each other. FIG. 20 is a graph showing one example of pressure characteristics in the air-cylinder apparatus 4110. As shown in the characteristics chart of FIG. 20, the air-cylinder apparatus 4110 can exhibit smooth characteristics for wider range of walking speed.

What is claimed is:

1. An air-cylinder apparatus for use in a prosthetic limb which is designed for assisting a bending motion and a stretching motion of a wearer's knee, said air-cylinder apparatus comprising a cylinder body of a cylindrical configuration whose one end portion is closed by a head part and the other end portion is closed by a bottom part, a piston disposed within said cylinder body and defining an interior of said cylinder body into a first chamber located on the head side and a second chamber located on the bottom side, a piston rod whose one end is integral with said piston and the other end extends outward from the head of said cylinder body so as to be connected with the prosthetic limb, a first passage for intercommunicating said first and second chambers and including a first check valve for permitting a flow of air from said first chamber towards said second chamber, and a second passage for intercommunicating said first and second chambers and including a constant throttle valve for normally restricting a flow of air from said second chamber towards said first chamber, in order to increase internal pressure of said second chamber when the knee is bent, said air-cylinder apparatus further comprising:

(A) division means having a recess or projection at a bottom part of said cylinder body and a counterpart projection or recess at one surface of said piston facing the bottom part and adapted to divide said second chamber on the bottom side into a plurality of chambers including a predetermined chamber confronting an opening leading for communication to said constant throttle valve; and (B) an auxiliary passage for communicating the plurality of chambers divided by said division means with said first chamber through a throttle valve.

2. An air-cylinder apparatus according to claim 1, wherein said throttle valve of said auxiliary passage is in communication with said first chamber via the predetermined chamber and said constant throttle valve.

3. An air-cylinder apparatus according to claim 1, wherein said division means includes a seal member for sealing said recess or projection to be engaged with each other.

4. An air-cylinder apparatus according to claim 2, wherein said second passage serves as a common passage for communicating the divided plural chambers with said first chamber.

5. An air-cylinder apparatus according to claim 1, wherein said second passage includes, in addition to said constant throttle valve, a second check valve for permitting a flow of air from said second chamber towards said first chamber.

6. An air-cylinder apparatus according to claim 1, wherein said throttle valves are fixed throttle valves each having a constant throttling amount.

7. An air-cylinder apparatus according to claim 1, wherein said second passage is disposed at said cylinder body.

8. An air-cylinder apparatus according to claim 7, wherein said first passage is disposed at either one of said piston and said cylinder body.

9. An air-cylinder apparatus according to claim 1, wherein the predetermined chamber is smaller in volume than the remaining chamber among the plural chambers obtained by division.

10. An air-cylinder apparatus according to claim 1, wherein the plural chambers obtained by division are concentrically arranged about a center axis of said piston.

* * * * *